United States Patent [19]

Krämer et al.

[11] 4,418,072
[45] Nov. 29, 1983

[54] DIASTEREOMERIC 1-(4-CHLOROPHENOXY)-1-(1-IMIDAZOLYL)-3,3-DIMETHYL-2-BUTANOL COMPOUNDS AND THEIR ANTIMYCOTIC USE

[75] Inventors: Wolfgang Krämer; Karl H. Büchel; Ingo Haller; Manfred Plempel, all of Wuppertal, Fed. Rep. of Germany

[73] Assignee: Bayer Aktiengesellschaft, Leverkusen, Fed. Rep. of Germany

[21] Appl. No.: 247,413

[22] Filed: Mar. 25, 1981

Related U.S. Application Data

[63] Continuation-in-part of Ser. No. 95,000, Nov. 16, 1979, abandoned.

[30] Foreign Application Priority Data

Nov. 18, 1978 [DE] Fed. Rep. of Germany ....... 2850057

[51] Int. Cl.³ .................. A61K 31/415; C07D 233/60
[52] U.S. Cl. ................................. 424/273 R; 548/341
[58] Field of Search ..................... 548/341; 424/273 R

[56] References Cited

U.S. PATENT DOCUMENTS 3,940,414 2/1976 Kramer et al. ...................... 548/341
3,968,229 7/1976 Krämer et al. ................. 424/273 R

*Primary Examiner*—Richard Raymond
*Assistant Examiner*—Natalia Harkaway
*Attorney, Agent, or Firm*—Sprung, Horn, Kramer & Woods

[57] ABSTRACT

The invention relates to diastereoisomeric 1-(4-chlorophenoxy)-1-(1-imidazolyl)-3,3-dimethyl-2-butanol and methods for its preparation. Also included in the invention are compositions containing said diastereoisomeric 1-(4-chlorophenoxy)-1-(1-imidazolyl)-3,3-dimethyl-2-butanol and methods for the use of said compound and compositions as antimycotic agents.

9 Claims, No Drawings

DIASTEREOMERIC 1-(4-CHLOROPHENOXY)-1-(1-IMIDAZOLYL)-3,3-DIMETHYL-2-BUTANOL COMPOUNDS AND THEIR ANTIMYCOTIC USE

This is a continuation-in-part application of Ser. No. 095,000, filed Nov. 16, 1979, now abandoned.

The present invention relates to certain new diastereomeric 1-(4-chlorophenoxy)-1-(1-imidazolyl)-3,3-dimethyl-2-butanol compounds, to a process for their production and to their use as antimycotic agents.

It has already been disclosed that the diastereomer mixture of 1-(4-chlorophenoxy)-1-(1-imidazolyl)-3,3-dimethyl-2-butanol has a generally antimycotic action (compare DE-OS (German Published Specification) No. 2,333,355 and U.S. Pat. No. 3,968,229.

According to the present invention there are provided compounds which are the enantiomer pair of the diastereomeric form A (as hereinafter defined) of 1-(4-chlorophenoxy)-1-(1-imidazolyl)-3,3-dimethyl-2-butanol, of the formula

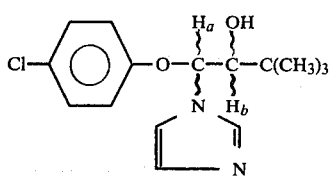

and salts thereof.

The compounds of the invention have powerful antimycotic properties.

For explanation, the following should be noted: Compounds with two asymmetric carbon atoms can exist in the two diasteromeric forms of threo and erythro. Because the absolute configuration is as yet undetermined, the allocation in the compound according to the invention is possible only with reservations, which is expressed by the wavy lines in formula (I). A distinction may be made between form A and form B, which can be unambiguously characterised by their physico-chemical properties. "Diastereomeric form A," the more hydrophilic form, is characterised by smaller coupling constants for the protons $H_{(a)}$ and $H_{(b)}$ in the NMR spectrum.

According to the present invention there is further provided a process for the production of compounds of the present invention in which 1-(4-chlorophenoxy)-1-(1-imidazolyl)-3,3-dimethyl-2-butanone of the formula

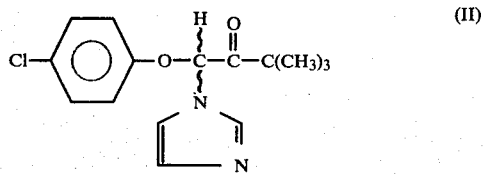

is reduced stereoselectively with a secondary alcholate in the presence of a diluent, and is, if desired, thereafter converted into a salt by reaction with an acid. Among the new salts of diastereomeric form A of 1-(4-chlorophenoxy)-1-(1-imidazolyl)-3,3-dimethyl-2-butanol, those salts that are pharmaceutically acceptable are particularly important and are preferred.

Surprisingly, the diastereomeric form A, according to the invention, of 1-(4-chlorophenoxy)-1-(1-imidazolyl)-3,3-dimethyl-2-butanol of the formula (I) exhibits a considerably better, therapeutically usable activity than the corresponding diastereomer mixture known from the state of the art. The substances according to the invention thus represent a valuable advance in pharmacy. On the basis of the known state of the art, it could in no way be expected that the form A, according to the invention, of the formula (I) is distinguished by very good antimycotic properties, whilst the analogous form B of this compound has only a weak activity as an antimycotic agent.

If, in addition to 1-(4-chlorophenoxy)-1-(1-imidazolyl)-3,3-dimethyl-2-butanone, aluminium isopropylate is used as a starting substance, the course of the reaction can be represented by the following equation:

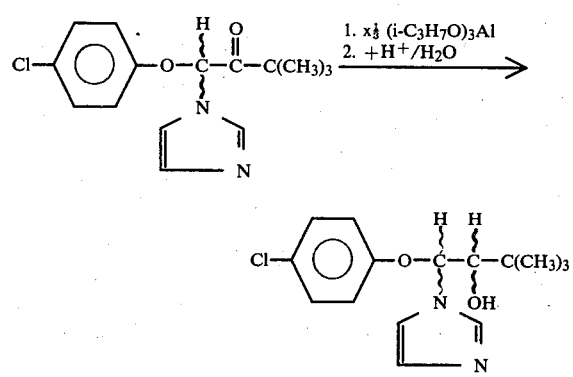

The ketone of the formula (II) to be used as a starting substance is known (compare DE-OS (German Published Specification) No. 2,105,490 (U.S. Pat. Nos. 3,903,287 and 3,812,142)). It is obtained by the process described in this reference, by reacting a 1-(4-chlorophenoxy)-1-halogeno-3,3-dimethyl-2-butanone with imidozole, if appropriate in the presence of an acid-binding agent, at temperatures between 60° and 120° C.

The reduction according to the invention is carried out with the aid of secondary alcoholates (preferably alkanolates having up to 4 carbon atoms and cycloalkanol having 5 to 7 ring members). These include, preferably the secondary alcoholates of aluminium, such as, more preferably, aluminium isopropylate, aluminium sec. butylate and aluminium cyclohexylate. Preferred diluents which can be used for the reaction according to the invention are inert organic solvents. These include, preferably, alcohols (such as alkanols having up to 5 carbon atoms), such as, in particular isopropanol and sec.-butanol.

A particularly high stereoselectivity is obtained for the reduction by using aluminium isopropylate in isopropanol. The reaction temperatures can be varied within a substantial range in the process according to the invention. Preferably, the reaction is carried out between 80° and 120° C., more preferably at the boiling point of the solvent. In carrying out the reaction according to the invention 0.35 to 1.5 mols of secondary alcoholate are preferably employed per 1 mol of the ketone of the formula (II).

In order to isolate the compound of the formula (I), the excess solvent is removed by distillation in vacuo and the aluminium compound formed is decomposed with dilute sulphuric acid or sodium bisulphate solution. Further working up is carried out in the customary manner.

According to a preferred embodiment, a procedure is appropriately followed in which the ketone of the formula (II) is reduced in the presence of the corresponding form A, whereupon the stereoselectively of the reduction is shifted further in favour of the desired form A. In this procedure, 0.5 mol of the corresponding diastereomeric form A and 0.5 mol of secondary alcoholate are preferably employed per 1 mol of the ketone of the formula (II). All the acids which give rise to pharmaceutically acceptable salts can be used for such salt preparation. These acids include, preferably, hydrogen halide acids, such as, for example, hydrochloric acid and hydrobromic acid, especially hydrochloric acid, and furthermore phosphoric acid, nitric acid, sulphuric acid, monofunctional and bifunctional carboxylic acids and hydroxycarboxylic acids, such as, for example, acetic acid, maleicacid, succinic acid, fumaric acid, tartaric acid, citric acid, salicylic acid, sorbic acid and lactic acid, and sulphonic acids, such as, for example, p-toluenesulphonic acid and 1,5-naphthalenedisulphonic acid.

The salts of the compound of the formula (I) can be obtained in a simple manner by customary salt formation methods, for example by dissolving the compound of the formula (I) in a suitable inert solvent and adding the acid, for example hydrochloric acid, and they can be isolated in a known manner, for example by filtration, and if appropriate purified by washing with an inert organic solvent. The compounds of the formula (I) according to the invention, and their acid addition salts, display antimicrobial actions, in particular antimycotic actions. They possess a very broad antimycotic action spectrum, especially against dermatophytes and blastomyces as well as biphase fungi, for example against species of Candida, such as *Candida albicans*, varieties of Epidermophyton, such as *Epidermophyton floccosum*, varieties of Aspergillus, such as *Aspergillus niger* and *Aspergillus fumigatus*, varieties of Trichophyton such as *Trichophyton mentagrophytes*, varieties of Microsporon, such as *Microsporon felineum* and varieties of Penicillium, such as *Penicillium commune*. This list of microorganisms in no way implies a limitation of the germs which can be combated but is only illustrative.

Examples which may be mentioned of fields of application in medicine are: dermatomycoses and systemic mycoses caused by *Trichophyton mentagrophytes* and other varieties of Trichophyton, varieties of Microsporon, *Epidermophyton floccosum*, blastomyces and biphase fungi as well as moulds.

As stated above, the invention also relates to the use in human and veterinary medicine of the compounds of the invention.

The present invention provides a pharmaceutical composition containing as active ingredient a compound of the invention in admixture with a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile and/or physiologically isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this specification means physically discrete coherent portions suitable for medical administration. "Medicament in dosage unit form" as used in this specification means physically discrete coherent units suitable for medical administration each containing a daily dosage or a multiple (up to four times) or submultiple (down to a fortieth) of a daily dose of the compound of the invention in association with a carrier and/or enclosed with an envelope. Whether the medicament contains a daily dose of, for example, a half, a third or a quarter of a daily dose will depend on whether the medicament is to be administered once or, for example, twice, three times or four times a day respectively. The pharmaceutical compositions according to the invention may, for example, take the form of ointments, gels, pastes, creams, sprays (including aerosols), lotions, suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) absorptive carriers, e.g. kaolin and bentonite; (i) lubricants, e.g. talc, calcium and magnesium stearate and solid polyethyl glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble diluents, such as polyethylene glycols and fats (e.g. cocoa oil and high esters (e.g. $C_{14}$-alcohol with $C_{16}$-fatty acid)) or mixtures of these diluents. The pharmaceutical compositions which are ointments, pastes, creams and gels can, for example, contain the usual diluents, e.g. animal and vegetable fats, waxes, paraffins, starch, tragacanth, cellulose derivatives, polyethylene glycols, silicones, bentonites, silicic acid, talc, and zinc oxide or mixtures of these substances.

The pharmaceutical compositions which are powders and sprays can, for example, contain the usual diluents, e.g. lactose, talc, silicic acid, aluminium hydroxide, calcium silicate, and polyamide powder or mixtures of these substances. Aerosol sprays can, for example, contain the usual propellants, e.g. chlorofluorohydrocarbons.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzonate, propylene glycol, 1,3-butylene glycol, dimethylformamide, oils (for example, ground nut oil), glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic. The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin). The pharmaceutical compositions according to the invention generally contain from 0.1 to 99.5%, usually from 0.5 to 95% of the active ingredient by weight of the total composition. In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills, dragees capsules, suppositories and ampoules. Some of these forms may be made up for delayed release of the active ingredient. Some, such as capsules, include a protective envelope which renders the portions of the medicament physically discrete and coherent. The preferred daily dose for administration of the medicaments of the invention is 2.5 to 10 g of active ingredient.

The product of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets). This invention further provides a method of combating (including prevention, relief and cure of) the above-mentioned diseases in warm-blooded animals, which comprises administering to the animals a compound of the invention alone or in admixture with a diluent or in the form of a medicament according to the invention.

It is envisaged that these active compounds will be administered perorally, parenterally, (for example intramuscularly, intraperitoneally, subcutaneously and intravenously), rectally or locally, preferably parenterally, especially intravenously. Preferred pharmaceutical compositions and medicaments are therefore those adapted for administration such as parenteral administration. Administration in the method of the invention is preferably parenteral administration.

In general it has proved advantageous to administer amounts of from 10 mg to 300 mg/kg, preferably 50 mg to 200 mg/kg, of body weight per day to achieve effective results. Nevertheless, it can at times be necessary to deviate from those dosage rates, and in particular to do so as a function of the nature and body weight of the human or animal subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above-mentioned minimum dosage rate, whilst other cases the upper limit mentioned must be exceeded to achieve the desired results. Where larger amounts are administered it can be advisable to divide these into several individual administrations over the course of the day.

The following Examples A, B and C illustrate the in-vitro and in vivo activity of compounds of the present invention.

EXAMPLE A

Antimycotic in-vitro activity

Description of the experiment:

The in-vitro activity, measured with the aid of the minimum inhibitory concentrations, was determined in an agar dilution test. With the aid of an automatic inoculating device, samples of the germ suspensions were applied in the form of drops to series of Kimmig agar plates which contained the appropriate active compound concentrations dissolved in agar. The inoculum was $2-5 \times 10^3$ of fungi particle per inoculation spot. In the case of yeasts, the incubation time was 24 hours, and in the case of dermatophytes 96 hours: incubation temperature 27° C. In this experimental arrangement, the enantiomer mixture, according to the invention, of the A forms showed considerably better minimum inhibitory concentrations against numerous yeasts, above all Candida species, and dermatophytes than the known diastereomer mixture. The enantiomer mixture of form B proved to have only a weak activity.

EXAMPLE B

Antimicrobial in-vivo activity (oral) in *candidosis* of mice

Mice of the SPF-CF$_1$ type are infected intravenously with $1-2 \times 10^6$ logarithmically growing Candida cells suspended in physiological sodium chloride solution. The animals are treated orally twice daily over a period of 5 days with dosages of 12.5/25/50/100 mg/kg of body weight.

Result

A significant gradation in the therapeutic activity can be observed at all the dosages tested:

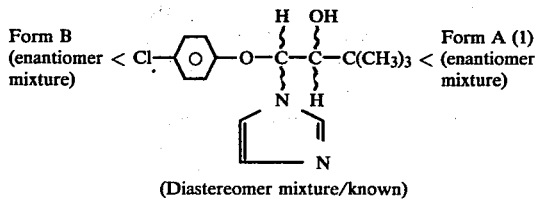

(Diastereomer mixture/known)

EXAMPLE C

Antimicrobial in-vivo activity (local and oral) using experimental *trichophytia* of guinea pigs as an example Description of the experiment White guinea pigs of the Pirbright-white race are infected, on their shaven, non-scarified backs, with a microconidia and macroconidia suspension of *Trichophyton mentagrophytes*. The typical pattern of dermatophytosis with reddening, scaling and loss of hair up to total integumentary defect. At the point of infection develops within 12 days after infection in the case of untreated animals. The infected animals are (a) treated locally once daily, starting on the 3rd day after infection, with a 1% strength solution of the preparations according to the invention (in dimethylsulphoxide/glycerol = 1:4); or (b) treated orally once daily, starting on the day of infection, with 25 mg/kg of body weight of the preparations according to the invention (in aqueous solution).

The enantiomer mixture, according to the invention, of the form A proved to have a good activity in the case of local and oral therapy; the enantiomer mixture showed no action, whilst the known diastereomer mixture had a trace of action.

The following Examples illustrate the production of compounds of the present invention.

EXAMPLE 1

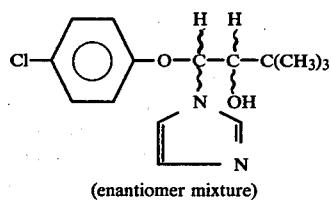

(enantiomer mixture)

10 kg (34.16 mols) of 1-(4-chlorophenoxy)-1-(1-imidazolyl)-3,3-dimethyl-2-butanone, 3.44 kg (16.74 mols) of aluminium isopropylate and 28 l of isopropanol are heated in a 40 l glass kettle at a bath temperature of 98°–102° C. for 16 hours. 12 l of solvent are thereby distilled off. 20 l of isopropanol are added to the product which presipitates on cooling the reaction solution, the mixture is heated up to 70° C. and drained off hot into a 100 l enamel kettle and a solution of 6.91 kg (57.6 mols) of sodium bisulphate in 32 l of water are added, whilst stirring. The mixture is stirred for 8 hours and then filtered over clay filters. The moist residue is suspended in 13 l of ethanol, and a solution of 10.3 l of 10% strength sodium hydroxide and 25.7 l of water is added. The mixture is stirred for 4 hours and filtered, 20.1 of water are added to the residue, the mixture is again filtered and the residue is dried. 7.5 kg (66.7% of theory) of pure threo form A (determined by gas chromatography) of 1-(4-chlorophenoxy)-1-(imidazolyl)-3,3-dimethyl-2-butanol of melting point 158°–159° C. are obtained. The pure erythro form B of 1-(4-chlorophenoxy)-1-(1-imidazolyl)-3,3-dimethyl-2-butanol has a melting point of 140°–142° C.

EXAMPLE 2

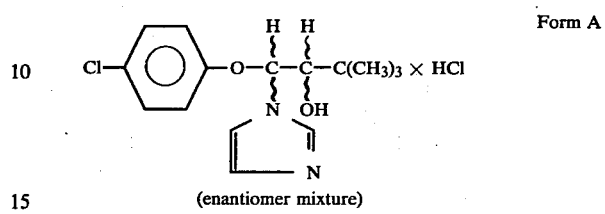

(enantiomer mixture)

The 7.5 kg of the pure form A of 1-(4-chlorophenoxy)-1-(1-imidazolyl)-3,3-dimethyl-2-butanol, obtained according to Example 1, are stirred in 37.5 l of 2 N hydrochloric acid. After adding 50 l of n-butanol, the mixture is stirred for 2.5 hours and the organic phase is seperated off, rinsed twice with 12.5 l of 2 N hydrochloric acid and concentrated.

The residue is suspended in 10 l of methylene chloride in the cold and filtered off. The residue is rinsed with 6 l of methylene chloride and dried at 50° C. in a circulating air oven. 8 kg (95% of theory) of the pure form A (determined by gas chromatography) of 1-(4-chlorophenoxy)-1-(1-imidazolyl)-3,3-dimethyl-2-butanol hydrochloride of melting point 236°–237° C. are obtained.

The present invention also comprises pharmaceutically acceptable bioprecursors of the active compounds of the present invention.

For the purposes of this specification the term 'pharmaceutically acceptable bioprecursor' of an active compound of the invention means a compound having a structural formula different from the active compound but which nonetheless, upon administration to an animal or human being is converted in the patient's body to the active compound.

What is claimed is:

1. A compound which is the diastereomeric form A of 1-(4-chlorophenoxy)-1-(1-imidazolyl)-3,3-dimethyl-2-butanol of the formula

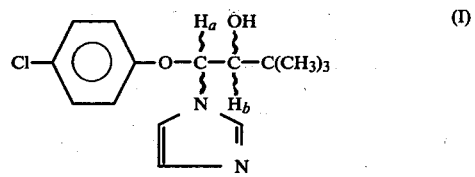

or its hydrochloride, said diastereomeric form A of 1-(4-chlorophenoxy)-1-(1-imidazolyl)-3,3-dimethyl-2-butanol having a melting point of 158°–159° C. and its hydrochloride having a melting point of 236°–237° C.

2. An antimycotic pharmaceutical composition containing as an active ingredient an antimycotically effective amount of a compound according to claim 1 in admixture with an inert diluent.

3. A pharmaceutical composition of claim 2 in the form of a sterile or physiologically isotonic aqueous solution.

4. A composition according to claim 2 or 3 containing from 0.5 to 95% by weight of the said active ingredient.

5. A medicament in dosage unit form comprising an antimycotically effective amount of a compound according to claim 1 together with an inert pharmaceutical carrier.

6. A medicament of claim 5 in the form of tablets, pills, dragees, capsules, ampoules, or suppositories.

7. A method of combating mycoses in warm-blooded animals which comprises administering to an animal in need thereof, an antimycotically effective amount of an active compound according to claim 1 either alone or in admixture with a diluent or in the form of a medicament.

8. A method according to claim 7 in which the active compound is administered in an amount of 50 to 200 mg/kg body weight per day.

9. A method according to claim 7 or 8 in which the active compound is administered parenterally.

* * * * *